United States Patent [19]

Telfer

[11] Patent Number: 4,829,837
[45] Date of Patent: May 16, 1989

[54] ROBOTIC LIQUID SEPARATION SENSING USING A CANNULA

[75] Inventor: Alexander Telfer, Houston, Tex.

[73] Assignee: Shell Oil Company, Houston, Tex.

[21] Appl. No.: 149,276

[22] Filed: Jan. 28, 1988

[51] Int. Cl.[4] .......................... G01N 1/14; H01G 5/28
[52] U.S. Cl. ................................. 73/863.01; 73/304 C; 361/284
[58] Field of Search ........... 73/863.01, 864.23, 864.24, 73/864.21, 864.22, 290 R, 304 C; 422/100, 81; 324/61 R, 61 QS; 361/284, 280, 278; 340/620, 603

[56] References Cited

U.S. PATENT DOCUMENTS

| | | | |
|---|---|---|---|
| 3,545,271 | 12/1970 | Amis et al. | 361/284 |
| 3,588,859 | 6/1971 | Petree | 361/284 |
| 3,770,020 | 11/1973 | Tamura et al. | 73/304 C |
| 3,894,438 | 7/1975 | Ginsberg | 73/863.01 |
| 4,165,641 | 8/1979 | Pomerantz et al. | 73/304 C |
| 4,240,028 | 12/1980 | Davis, Jr. | 324/61 QS |
| 4,325,909 | 4/1982 | Coulter et al. | 73/864.24 |
| 4,399,711 | 8/1983 | Klein | 422/100 |
| 4,568,874 | 2/1986 | Kramer et al. | 361/284 |

FOREIGN PATENT DOCUMENTS 0108754 6/1985 Saudi Arabia ...................... 422/100

Primary Examiner—Michael J. Tokar
Assistant Examiner—Robert R. Raevis

[57] ABSTRACT

Robotic liquid separation operates independently of liquid volume, viscosity, or optical characteristics, by sensing changes in the dielectric constant of the liquid as it is being drawn through a cannula. The cannula has electrodes which form a sensing capacitor for detecting the changes in the liquid dielectric constant as the liquid is drawn therethrough.

5 Claims, 1 Drawing Sheet

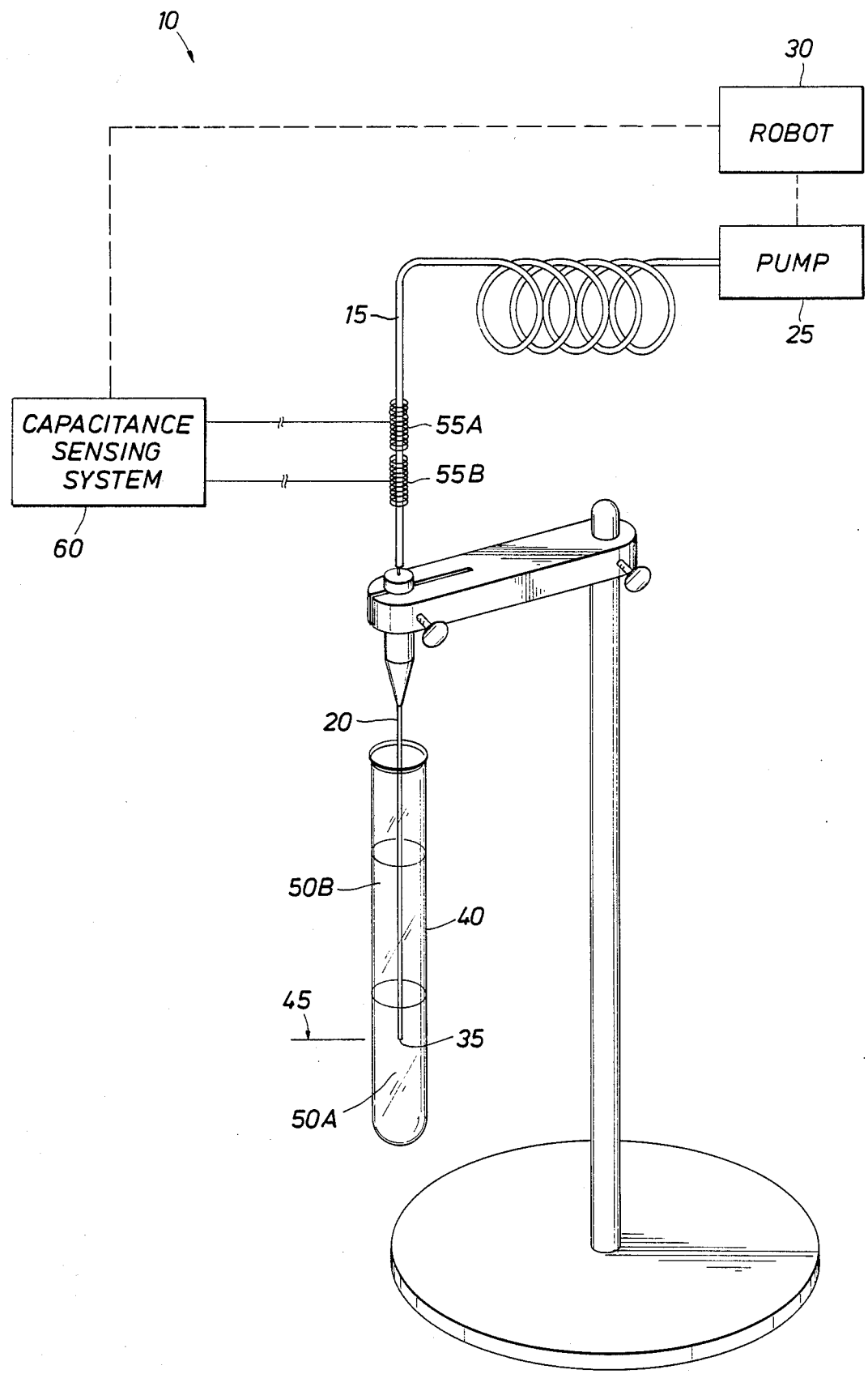

ROBOTIC LIQUID SEPARATION SENSING USING A CANNULA

BACKGROUND OF THE INVENTION

The present invention relates to robotics systems for use in automated laboratory applications, and more particularly to a liquid separation device which is particularly well suited for such applications as automated analytical laboratory systems. Frequently, for example, immiscible liquids must be separated from a container, such as a test tube, but the volumes of the liquids to be separated are unknown. The present invention detects when the removal device has concluded withdrawing the target liquid independently of the volume withdrawn or the time required therefor.

Automation in analytical laboratories is not, of itself, a new concept, but instead has been widely practiced for many years. More recently, it has appeared mainly in the form of microprocessor-controlled analytical instrumentation with dedicated hardware, such as auto samplers, continuous flow systems, and computerized data collection, calculation, and report generation facilities. The very recent past has seen important improvements wherein laboratory automation has been extended by the use of robotics, combined with programmable computers, to new tasks which include sample preparation, and even entire analytical determinations. The first such robotic system was introduced in 1982 by Zymark Corporation (Hopkinton, Mass.). As experience has been gained with these systems, they have been successfully applied to ever more sophisticated laboratory operations, and the number of accessory components for specific tasks has grown accordingly. Understandably, however, there continues to be a great need for accessory modules and equipment which can provide sophisticated support operations in a robot-friendly manner. Tasks which are so trival for a human operator that they go essentially unnoticed may prove to be all but insurmountable for a robotics system. Sometimes the most trival and routine manual operations turn out to be the most intransigent when efforts are made to perform them with robot-friendly modules and sensors. As a result, modules and sensors for performing many important tasks are still not yet commercially available.

An example in which accessories are available, but which have certain very definite limitations, has to do with withdrawing or removing liquids from a vessel such as a test tube, in the presence of other usually immiscible liquids. Due to differences in density, the liquids will ordinarily be separated. With a typical prior art system, a photocell will be positioned at the height down to which the heavier liquid is to be drawn. A cannula is then inserted down at least to that level and the heavier liquid is withdrawn through the cannula until the optical sensor detects a change in the optical characteristics of the liquid. This approach, which can also be used with a common solvent where separation has been achieved with centrifugation, is very effective, reliable, and relatively inexpensive when the respective liquids have distinguishing optical properties such as color and/or opacity. When such differences are absent, it is often convenient to add a selectively soluble dye so that adequate differences in optical properties can be artificially but harmlessly provided.

Of course, this still leaves a great number of situations in which optical separation is either inconvenient, or in some cases all but prohibited, due to the circumstances involved. In such cases, particularly when dealing with immiscible liquids, the interface between the liquids will usually be readily visible to a human operator, but the task is then anything but trivial for a robotics system.

A need therefore remains for a robotic separation sensor for use in combination with a cannula liquid delivery system for detecting when a liquid being delivered through the system is changed to another type of liquid, independently of such properties of the liquid as volume, viscosity, optical characteristics, or the time required for the liquid to be delivered. Such a system should accurately detect when the liquid has been withdrawn from the target container to the desired level, preferably based on the actual properties of the liquids involved in the procedure, without alteration such as the addition of foreign substances (dyes, etc.).

SUMMARY OF THE INVENTION

The present invention meets the above needs and purposes with a new and improved liquid separation sensor for use in combination with a cannula liquid delivery system, in which capacitance effects are employed for detecting when the liquid being delivered through the system is changed to another type of liquid. Advantageously, therefore, the invention provides sensitive detection of the change in the liquid independently of such properties of the liquids as volume, viscosity, optical characteristics, or the time required for the liquid to be delivered.

In the preferred embodiment, the cannula is provided with at least a small link of conduit which is substantially non-metallic. Typically, this constitutes a length of plastic tubing in the liquid path in the cannula liquid delivery system. A pair of electrodes is located substantially adjacent this non-metallic conduit portion, preferably surrounding the conduit, to form a sensing capacitor. The sensing capacitor electrodes, in turn, are connected to a capacitance sensing means for detecting changes in the dielectric constants of liquids passing the electrodes in the non-metallic conduit portion.

In the preferred embodiment, the liquids being moved through the cannula delivery system are moved by a reversible pump, and the control means for the cannula liquid delivery system includes means for reversing the pump when the change in the liquid is detected. This provides for expelling the new liquid from the cannula delivery system when the pump is reversed just long enough to expel a volume of liquid equal to the volume of the system between its intake and the electrodes.

It will be understood, of course, that some liquids which naturally separate will have similar dielectric constants. However, the more common situation encountered in laboratory analytical procedures involves liquid systems with significantly different dielectric constants. Typically, it is the separation of a water-based solution from an oil-based solution. In those typical cases, the present invention is especially advantageous because the heavier liquid can be withdrawn from the target vessel down to the height of the cannula inlet easily and accurately, and without needing to alter the liquids in any manner, such as contaminating them with a selectively soluble, optically active dye.

It is therefore an object of the present invention to provide a new and improved method and apparatus for sensing liquid separation which can be used in combination with a cannula liquid delivery system for detecting when a liquid being delivered through the system has changed to another type of liquid; such a method and apparatus which sense the change in the liquid independently of such properties as volume, viscosity, optical characteristics, or the time required for the liquid to be delivered; in which the change in the liquid can be sensed without the need to introduce foreign substances into one or more of the liquids; which includes a substantially non-metallic conduit portion in the liquid path in the cannula liquid delivery system; in which first and second electrodes are located substantially adjacent the non-metallic conduit portion and substantially adjacent each other; in which the electrodes form a sensing capacitor for detecting changes in the dielectric constants of liquids passing therepast in the non-metallic conduit portion; in which a capacitance sensing means is connected to the electrodes for detecting such changes in the dielectric constants of these liquids as they are delivered through the cannula system, and thereby detects when a liquid being delivered through the cannula system has changed to another type of liquid, independently of other properties of the liquid; in which the electrodes may be of a type which entirely surround the non-metallic conduit portion; which may further include a reversible pump in the cannula liquid delivery system for moving such liquids therethrough; in which means may be provided for reversing the pump upon detection of such a change in the liquid to expel a predetermined volume of liquid from the cannula liquid delivery system which is a volume substantially equal to the volume of the system between its intake and the electrodes; and to accomplish the above objects and purposes in an inexpensive, uncomplicated, durable, versatile, and reliable method and apparatus, inexpensive to manufacture and implement, and widely suited to the widest possible utilization in robot-friendly procedures and environments.

These and other objects and advantages of the invention will be apparent from the following description, the accompanying drawing, and the appended claims.

BRIEF DESCRIPTION OF THE DRAWING

The drawing figure is a schematic and diagrammatic view in perspective of a liquid separation sensing system according to the present invention used in conjunction with a cannula liquid delivery system.

DESCRIPTION OF THE PREFERRED EMBODIMENT

With reference to the drawing, the new and improved liquid separation sensor for use in combination with a cannula liquid delivery system for detecting when a liquid being delivered through the system has changed to another type of liquid, and the method therefor according to the present invention, will be described. The drawing figure shows a cannula liquid delivery system 10 in which a non-metallic conduit 15 connects a cannula 20 to a reversible pump 25 under control of the robotics system 30. The bottom 35 of the cannula 20 is inserted into a liquid containing vessel, such as a test tube 40, to a target depth or level 45 (which may or may not be at the bottom of the vessel 40) down to which it is desired to draw the heavier or denser liquid 50A, on top of which is floating the lighter or less dense liquid 50B.

Adjacent (in the preferred embodiment, surrounding) the non-metallic conduit 15 is a pair of electrodes 55A and 55B connected to a capacitance sensing system 60, which in turn is connected to the robotics system 30. Suitable capacitance measuring equipment for the capacitance sensing or electronics system 60 is readily available, an example being Amprodux Model X4, ML15 (Amprodux Inc., New York, N. Y.).

The operation of the invention under control of a robotics system then proceeds as follows, it being understood that the invention could also be used manually as desired. In this case, the robot arm (not shown) places the liquid containing vessel, such as test tube 40, in position at the location of the cannula 20. The cannula 20 is then positioned within the vessel 40 such that the bottom of the cannula 35 is at the target depth or level 45. This is ordinarily accomplished either by lifting the test tube 40 to the proper height, or lowering the cannula 20 into the test tube after the test tube has been placed in a holder (not shown) at a predetermined height thereunder. The pump 25 is then actuated to withdraw the liquid 50A from the test tube 40. The electrodes 55A and 55B, forming a capacitor for the capacitance sensing system 60, operate therewith to detect the dielectric constant of the liquid 50A as it passes through conduit 15. When the lighter liquid 50B reaches the target level 45, the liquid being withdrawn will change and the dielectric constant of the liquid 50B will then be detected by the capacitance electrodes 55A and 55B and the capacitance sensing system 60. This provides an immediate indication that there is a change in the liquid being delivered through the cannula system to another type of liquid, independently of other properties of the liquid such as volume, viscosity, optical characteristics, or the time required for the liquid to be delivered down to the target level 45.

At this point, several options present themselves to the operator. If the objective of the procedure is to draw the interface between the liquids down to the target depth or level 45, which is typically the case, it will be desirable and the customary practice to take into account the volume of the cannula delivery system between the bottom or inlet 35 of the cannula 20 and the electrodes 55A and 55B. Otherwise, the target depth or level will be lower than the level at which the lighter liquid 50B first entered the cannula 20, in an amount related to the internal volume of the cannula and the non-metallic conduit 15 between the cannula inlet 35 and the electrodes 55A and 55B. Compensation is easily provided, however, by setting the target level 45 lower by an amount equivalent to that volume, and then when the lighter liquid 50B is detected, reversing the pump 25 for a known time based upon the known rate of the pump, to expel the volume of the lighter liquid 50B which has been drawn into the cannula system up to the electrodes 55A and 55B.

As may be seen, therefore, the present invention has numerous advantages. Principally, it provides a very reliable, time-independent method and apparatus to control a robot-friendly cannula liquid delivery or separation system. In an uncomplicated yet highly effective and reliable manner, the present invention accomplishes a task which, for a human operator, is trivial but for a robotics system has proven to be extremely difficult to perform for liquids which do not possess obvious optical differences, unless the procedure can tolerate contamination of at least one of those liquids with a selectively soluble dye. Due to the economy, versatility, and effectiveness of the present invention, it is expected that it will find ready application in a great variety of robotics analysis applications.

Accordingly, while the methods and forms of apparatus herein described constitute preferred embodiments of this invention, it is to be understood that the invention is not limited to these precise methods and forms of apparatus, and that changes may be made therein without departing from the scope of the invention.

What is claimed is:

1. A liquid separation sensor for use in combination with a cannula liquid delivery system for detecting when a liquid being delivered through the system has changed to another type of liquid, independently of such properties of the liquid as volume, viscosity, optical characteristics, or the time required for the liquid to be delivered, comprising:
   (a) a substantially non-metallic conduit portion in the liquid path in the cannula liquid delivery system;
   (b) a first electrode located substantially adjacent said non-metallic conduit portion;
   (c) a second electrode located substantially adjacent said first electrode and also substantially adjacent said non-metallic conduit portion;
   (d) said electrodes being configured to form a sensing capacitor for detecting changes in the dielectric constants of liquids passing therepast in said non-metallic conduit portion;
   (e) capacitance sensing means connected to said electrodes for detecting such changes in the dielectric constants of such liquids as the liquids are delivered through the cannula system, and thereby detecting when a liquid being delivered through the cannula system has changed to another type of liquid, independently of other properties of the liquid;
   (f) a reversible pump disposed in the cannula liquid delivery system for moving said liquids therethrough; and
   (g) means for reversing said pump upon detection of such a change in the liquid to expel a predetermined volume of liquid from the cannula liquid delivery system substantially equal to the volume of the system between its intake and said electrodes.

2. The sensor of claim 1 wherein said electrodes each substantially surround a portion of said non-metallic conduit portion.

3. A liquid separation sensor for use in combination with a cannula liquid delivery system for detecting when a liquid being delivered through the system has changed to another type of liquid, independently of such properties of the liquid as volume, viscosity, optical characteristics, or the time required for the liquid to be delivered comprising:
   (a) a substantially non-metallic conduit portion in the liquid path in the cannula liquid delivery system;
   (b) a first electrode substantially surrounding a first portion of said non-metallic conduit portion;
   (c) a second electrode substantially surrounding a second portion of said non-metallic conduit portion, said second electrode located substantially adjacent said first electrode;
   (d) said electrodes being configured to form a sensing capacitor for detecting changes in the dielectric constants of liquids passing therepast in said non-metallic conduit portion;
   (e) capacitance sensing means connected to said electrodes for detecting such changes in the dielectric constants of such liquids as the liquids are delivered through the cannula system, and thereby detecting when a liquid being delivered through the cannula system has changed to another type of liquid, independently of other properties of the liquid;
   (f) a reversible pump in the cannula liquid delivery system for moving such liquids therethrough; and
   (g) means for reversing said pump upon detection of such a change in the liquid to expel a predetermined volume of liquid from the cannula liquid delivery system substantially equal to the volume of the system between its intake and said electrodes.

4. A liquid separation method for use in combination with a cannula liquid delivery system for detecting when a liquid being delivered through the system has changed to another type of liquid, independently of such properties of the liquid as volume, viscosity, optical characteristics, or the time required for the liquid to be delivered, comprising:
   (a) positioning the electrodes of a sensing capacitor substantially adjacent a substantially non-metallic conduit portion in the liquid path in the cannula liquid delivery system, said conduit portion and the liquid flowing therethrough forming the dielectric of said sensing capacitor;
   (b) detecting changes in the dielectric constants of liquids passing between said electrodes in the non-metallic conduit portion as the liquids are delivered through the cannula system to detect when a liquid being delivered through the cannula system has changed to another type of liquid, independently of other properties of the liquid;
   (c) moving the liquids through the cannula liquid delivery system with a reversible pump; and
   (d) reversing the pump upon detecting of such a change in the liquid to expel a predetermined volume of liquid from the cannula liquid delivery system substantially equal to the volume of the system between its intake and the sensing capacitor.

5. A liquid separation method for use in combination with a cannula liquid delivery system for detecting when a liquid being delivered through the system has changed to another type of liquid, independently of such properties of the liquid as volume, viscosity, optical characteristics, or the time required for the liquid to be delivered, comprising:
   (a) positioning a sensing capacitor substantially adjacent a substantially non-metallic conduit portion in the liquid path in the cannula liquid delivery system, the sensing capacitor being comprised of a first electrode located substantially adjacent the non-metallic conduit portion, and a second electrode located substantially adjacent the first electrode and also substantially adjacent the non-metallic conduit portion, the electrodes each substantially surrounding a portion of the non-metallic conduit portion;
   (b) detecting changes in the dielectric constants of liquids passing the sensing capacitor in the non-metallic conduit portion as the liquids are delivered through the cannula system to detect when a liquid being delivered through the cannula system has changed to another type of liquid, independently of other properties of the liquid;
   (c) moving the liquids through the cannula liquid delivery system with a reversible pump; and
   (d) reversing the pump upon detection of such a change in the liquid to expel a predetermined volume of liquid from the cannula liquid delivery system substantially equal to the volume of the system between its intake and the electrodes.

* * * * *